(12) United States Patent
Morrison et al.

(10) Patent No.: US 8,535,659 B1
(45) Date of Patent: *Sep. 17, 2013

(54) NUTRITIONAL SUPPLEMENTS FOR PREGNANT WOMEN

(75) Inventors: John C. Morrison, Jackson, MS (US); Kenneth R. Greathouse, Los Altos, CA (US)

(73) Assignee: Argent Development Group, LLC, Mountain View, CA (US)

( * ) Notice: Subject to any disclaimer, the term of this patent is extended or adjusted under 35 U.S.C. 154(b) by 801 days.

This patent is subject to a terminal disclaimer.

(21) Appl. No.: 12/453,756

(22) Filed: May 21, 2009

Related U.S. Application Data

(60) Provisional application No. 61/128,824, filed on May 27, 2008.

(51) Int. Cl.
*A61K 9/48* (2006.01)
*A61K 38/43* (2006.01)
*A61K 9/68* (2006.01)
*A61K 47/00* (2006.01)
*A61K 31/70* (2006.01)
*A61K 31/525* (2006.01)
*A61K 31/51* (2006.01)
*A61K 31/355* (2006.01)
*A61K 31/07* (2006.01)
*A01N 59/16* (2006.01)
*A01N 59/20* (2006.01)
*A01N 45/00* (2006.01)

(52) U.S. Cl.
USPC .......... 424/94.1; 424/439; 424/441; 424/451; 424/408; 424/682; 424/630; 424/646; 424/641; 514/52; 514/167; 514/168; 514/251; 514/276; 514/458; 514/474; 514/725; 514/904

(58) Field of Classification Search
USPC .................. 424/94, 439, 441, 408, 682, 630, 424/641, 646; 514/52, 167, 168, 276, 458, 514/474, 725
See application file for complete search history.

(56) References Cited

U.S. PATENT DOCUMENTS

| | | | |
|---|---|---|---|
| 4,599,152 A | 7/1986 | Ashmead | |
| 4,814,177 A | 3/1989 | Walsdorf et al. | |
| 4,822,816 A | 4/1989 | Markham | |
| 4,830,716 A | 5/1989 | Ashmead | |
| 4,968,716 A | 11/1990 | Markham | |
| 5,070,085 A | 12/1991 | Markham | |
| 5,407,957 A | 4/1995 | Kyle et al. | |
| 5,492,938 A | 2/1996 | Kyle et al. | |
| 5,494,678 A | 2/1996 | Paradissis et al. | |
| 5,494,681 A | 2/1996 | Cuca et al. | |
| 5,516,925 A | 5/1996 | Pedersen et al. | |
| 5,869,084 A | 2/1999 | Paradissis et al. | |
| 5,895,652 A | 4/1999 | Giampapa | |
| 5,945,123 A | 8/1999 | Hermelin | |
| 5,948,443 A | 9/1999 | Riley et al. | |
| 5,973,224 A | 10/1999 | Fuchs et al. | |
| 5,976,568 A | 11/1999 | Riley et al. | |
| 6,197,329 B1 | 3/2001 | Hermelin et al. | |
| 6,214,379 B1 | 4/2001 | Hermelin | |
| 6,228,388 B1 | 5/2001 | Paradissis et al. | |
| 6,258,846 B1 | 7/2001 | Hermelin et al. | |
| 6,261,600 B1 | 7/2001 | Kirschner et al. | |
| 6,299,896 B1 | 10/2001 | Cooper et al. | |
| 6,352,713 B1 | 3/2002 | Kirschner et al. | |
| 6,361,800 B1 * | 3/2002 | Cooper et al. | 424/630 |
| 6,417,233 B1 | 7/2002 | Sears et al. | |
| 6,479,545 B1 | 11/2002 | Levinson et al. | |
| 6,488,956 B1 | 12/2002 | Paradissis et al. | |
| 6,495,177 B1 * | 12/2002 | deVries et al. | 426/72 |
| 6,569,857 B1 | 5/2003 | Hermelin et al. | |
| 6,576,666 B2 | 6/2003 | Hermelin et al. | |
| 6,660,293 B2 | 12/2003 | Giordano et al. | |
| 6,696,083 B1 | 2/2004 | Paradissis et al. | |
| 6,716,814 B2 | 4/2004 | Ericson et al. | |
| 6,814,983 B2 | 11/2004 | Giordano et al. | |
| 6,818,228 B1 | 11/2004 | Walsdorf et al. | |
| 6,863,904 B2 | 3/2005 | Giordano et al. | |
| 6,914,073 B2 | 7/2005 | Boulos et al. | |
| 6,953,588 B2 | 10/2005 | Cooper et al. | |
| 7,022,350 B2 | 4/2006 | Harvey et al. | |
| 7,112,609 B2 | 9/2006 | Hermelin et al. | |
| 7,205,007 B2 | 4/2007 | Lane | |
| 7,238,373 B2 | 7/2007 | Meyrowitz | |
| 7,390,509 B2 | 6/2008 | Giordano et al. | |
| 2004/0001817 A1 | 1/2004 | Giampapa | |
| 2005/0032740 A1 | 2/2005 | Venkataraman | |
| 2005/0037065 A1 * | 2/2005 | Kirschner et al. | 424/456 |
| 2005/0101670 A1 | 5/2005 | Hermelin et al. | |
| 2005/0106266 A1 | 5/2005 | Levinson et al. | |
| 2006/0115556 A1 * | 6/2006 | Foulger et al. | 426/72 |
| 2006/0121129 A1 | 6/2006 | Harvey et al. | |
| 2006/0134227 A1 | 6/2006 | Bortz et al. | |
| 2006/0153823 A1 | 7/2006 | Giordano et al. | |
| 2006/0153824 A1 | 7/2006 | Giordano et al. | |
| 2006/0217385 A1 | 9/2006 | Edwards et al. | |
| 2006/0217386 A1 * | 9/2006 | Edwards et al. | 514/251 |
| 2007/0231312 A1 * | 10/2007 | Muench et al. | 424/94.1 |

* cited by examiner

*Primary Examiner* — Taeyoon Kim
*Assistant Examiner* — Srikanth Patury
(74) *Attorney, Agent, or Firm* — Joseph I. Hirsch

(57) ABSTRACT

The present invention relates to different nutritional supplements to be administered to, or taken by, pregnant women during the first, second and third trimesters of pregnancy.

43 Claims, No Drawings

NUTRITIONAL SUPPLEMENTS FOR PREGNANT WOMEN

CROSS REFERENCE TO RELATED APPLICATION

This application claims priority from U.S. Provisional Application Ser. No. 61/128,824, filed May 27, 2008, the disclosure of which is incorporated herein by this reference.

FIELD OF THE INVENTION

The present invention relates to a set of different nutritional supplements to be administered to, or to be taken by, pregnant women during the first, second and third trimesters of pregnancy.

BACKGROUND OF THE INVENTION

The present invention relates to nutritional supplements to be administered to, or to be taken by, pregnant women. It is known that there are numerous deficiencies in the diets of pregnant women, particularly, but not exclusively, women of low and moderate incomes. More broadly, diets of people in general, and women in particular, in the United States are known to be poor, due in part to the prevalence of so-called "junk food", fast food, which is high in caloric content, but low in nutritional value, and the desire of many working people to eat prepared food after a long day at the office. For women of child-bearing age, the situation becomes worse when they become pregnant as what the fetus needs may not be provided by a given woman's normal daily dietary intake.

Many supplements have been proposed and are currently being marketed in the United States to overcome the nutritional deficiencies caused by such eating habits. For example, Hermelin et al. in U.S. Pat. Nos. 6,258,846, 6,576,666 and 7,112,609 describe in the Background of the Invention sections of their respective inventions, various formulations supplements, including prenatal formulations and supplements, that are (or were) on the market in the United States and contain various combinations of ingredients to supplement the nutrition, among others, of pregnant women. These include products known by the names Materna, Enfamil Natalins RX, Prenate Ultra, Niferex-PN, Niferex-PN Forte, Advanced Formula Zenate, Precare, and Natafort, all marketed by various companies that own the trademarked names of these products.

Riley U.S. Pat. Nos. 5,948,443 and 5,976,568 and Cooper et al. U.S. Pat. Nos. 6,299,896, 6,361,800 and 6,953,588 describe multi-vitamin and mineral supplements also including amounts of lycopene and co-enzyme Q10. These supplements are marketed as general wellness supplements for a wide range of people, but are not specifically described or marketed as being useful for pregnant women.

Paradissis et al. in U.S. Pat. Nos. 5,494,678 and 6,228,388 describe multi-vitamin and mineral supplements for pregnant women that are specifically tailored for the first, second and third trimesters of pregnancy, but contain one or more ingredients that we feel are not needed or are in amounts felt to be unnecessary.

Many of the supplements described above, and elsewhere in the literature, including those supplements currently on the market in the United States, contain a broad range of ingredients, many of which are not necessary to be administered to pregnant women. While they may not do any harm, in the sense that the body will eliminate in one way or another that which is not needed, there is a preference, and it is our desire, to set forth unique supplement formulations that have those, and only those, ingredients that serve necessary and beneficial purposes, particularly for pregnant women where the formulations of the present invention have differing amounts of ingredients for each of the three trimesters of pregnancy.

BRIEF SUMMARY OF THE INVENTION

The unique supplements of the present invention are particularly suited for being administered to, or to be taken by, pregnant women and are free of any other added vitamins and minerals, and other unnecessary ingredients, such as N-acetyl-cysteine.

The unique supplement formulations of the present invention are exemplified by the following specific embodiments.

In the broadest embodiment of the present invention, the nutritional supplement comprises a daily dose of:

about 2,000 IU (1.2 mg) to about 8000 IU (4.8 mg) of Vitamin A,
about 1 to about 5 mg of Vitamin $B_1$,
about 1 to about 15 mg of Vitamin $B_2$,
about 20 to about 50 mg of Vitamin $B_6$,
about 2 to about 12 mcg of Vitamin $B_{12}$,
about 20 to 200 mg of Vitamin C,
about 200 IU (5 mcg) to about 500 IU (12.50 mcg) of Vitamin $D_3$,
about 10 to about 40 mg of Vitamin E,
about 100 to about 500 mg of a lycopene-containing material,
about 50 to about 200 mg of co-enzyme Q10,
about 50 to about 250 mg of docosahexaenoic acid (DHA),
about 50 to about 100 mg of docusate sodium,
about 1 to 3 mg of copper,
about 1 to about 5 mg of folic acid,
about 30 to about 90 mg of elemental iron,
about 10 to about 100 mg of magnesium,
about 10 to about 30 mcg of selenium,
about 15 to about 30 mg of zinc, and
a pharmaceutically or nutritionally acceptable carrier therefor.

Within the ranges set forth above, various amounts of the ingredients can be selected, as shown, for example, in greater detail below, in providing specific formulations for use as the needs of a pregnant woman change during the course of the three trimesters of her pregnancy. The amounts of certain ingredients will remain constant throughout the three trimesters, while the amounts of other ingredients will vary, also as shown below.

In a particularly preferred embodiment of the present invention particularly suitable for administration during the first trimester of pregnancy, a nutritional supplement consists of a daily dose of:

about 2,500 IU (1.5 mg) of Vitamin A (as beta-carotene),
about 2 mg of Vitamin $B_1$,
about 3.4 mg of Vitamin $B_2$,
about 50 mg of Vitamin $B_6$,
about 2 mcg of Vitamin $B_{12}$,
about 60 mg of Vitamin C,
about 400 IU (10 mcg) of Vitamin $D_3$,
about 10 mg of Vitamin E,
about 100 mg of a 5% lycopene-containing material affording about 5 mg of actual lycopene,
about 200 mg of co-enzyme Q10,
about 100 mg of docosahexaenoic acid (DHA),
about 50 mg of docusate sodium,
about 2 mg of copper,
about 1 mg of folic acid, about 30 mg of elemental iron,
about 30 mg of magnesium,
about 15 mcg of selenium,
about 15 mg of zinc, and
a pharmaceutically or nutritionally acceptable carrier therefor.

In another particularly preferred embodiment of the present invention particularly suitable for administration during the second trimester of pregnancy, a, nutritional supplement consists of a daily dose of:
about 2,500 IU (1.5 mg) of Vitamin A (as beta-carotene),
about 2 mg of Vitamin $B_1$,
about 3.4 mg of Vitamin $B_2$,
about 25 mg of Vitamin $B_6$,
about 2 mcg of Vitamin $B_{12}$,
about 60 mg of Vitamin C,
about 400 IU (10 mcg) of Vitamin $D_3$,
about 20 mg of Vitamin E,
about 200 mg of a 5% lycopene-containing material affording about 10 mg of actual lycopene,
about 150 mg of co-enzyme Q10,
about 150 mg of docosahexaenoic acid (DHA),
about 75 mg of docusate sodium,
about 2 mg of copper,
about 2 mg of folic acid,
about 45 mg of elemental iron,
about 50 mg of magnesium,
about 15 mcg of selenium,
about 30 mg of zinc, and
a pharmaceutically or nutritionally acceptable carrier therefor.

In another particularly preferred embodiment of the present invention particularly suitable for administration during the third trimester of pregnancy, a nutritional supplement consists of a daily dose of:
about 2,500 IU (1.5 mg) of Vitamin A (as beta-carotene),
about 2 mg of Vitamin $B_1$,
about 3.4 mg of Vitamin $B_2$,
about 20 mg of Vitamin $B_6$,
about 2 mcg of Vitamin $B_{12}$,
about 60 mg of Vitamin C,
about 400 IU (10 mcg) of Vitamin $D_3$,
about 30 mg of Vitamin E,
about 100 mg of a 5% lycopene-containing material affording about 5 mg of actual lycopene,
about 150 mg of co-enzyme Q10,
about 200 mg of docosahexaenoic acid (DHA),
about 100 mg of docusate sodium,
about 2 mg of copper,
about 3 mg of folic acid,
about 60 mg of elemental iron,
about 50 mg of magnesium,
about 15 mcg of selenium,
about 30 mg of zinc, and
a pharmaceutically or nutritionally acceptable carrier therefor.

The preferred form of administration of the supplements of the present invention is oral dosage forms, preferably tablets for oral administration, taken once daily in the amounts set forth above in the morning along with breakfast or after any early morning nausea has passed. However, smaller tablets may be used if administration is desired to be twice daily, or three times daily, for example, at other or each mealtime, or after any pregnancy-induced nausea may have subsided. The tablets can be scored to be broken in half for ease of self-administration if desired, which is particularly appropriate with larger tablets, or chewable tablets can be used.

DETAILED DESCRIPTION OF THE INVENTION

Vitamin A plays an important role in maintaining the integrity of all epithelial tissues (skin/mucous membrane). It is also essential in the synthesis of retinal pigmentation and deficiency leads to a variety of ophthalmic problems. This vitamin is essential for normal fetal development and conversely deficiency leads to congenital malformations as well as fetal mortalities. The present invention includes about 2,000-8000 IU/day, preferably about 2500 IU (1.5 mg)/day, of Vitamin A, as beta-carotene, to supply the developing fetus with adequate amounts of this essential vitamin regardless of maternal diet. Each IU of beta-carotene corresponds to 0.6 mcg.

Vitamin $B_1$ is very important in red blood cell formation and all of the ingredients of fetal blood cells. Deficiency in the mother can result in acute fetal cardiac failure from significant anemia in the fetus. Since this vitamin is not ubiquitous in a normal diet, the present invention includes about 1 mg/day to about 5 mg/day of Vitamin $B_1$, preferably about 2 mg/per day, as thiamine, to enhance red blood cell formation.

The requirements for Vitamin $B_2$ increase during pregnancy. Deficiency has been associated with fetal malformation of the bony tissue and membranous skeleton, which precedes the cartilageous and osseous skeletons. A deficiency of Vitamin $B_2$ is also linked to hyperemesis gravidarum and an increased incidence of growth restriction and preterm delivery in the fetus. Maternal deficiency of Vitamin $B_2$ is associated with stomatitis, glossitis and cheilosis. The present invention includes about 1 mg day to about 15 mg/day, preferably about 3.4 mg/day, of Vitamin $B_2$, as riboflavin, to mitigate any deficiency of this vital material during pregnancy.

Vitamin $B_6$ (pyridoxine) is used by obstetricians to combat hyperemesis of pregnancy. During pregnancy $B_6$ levels in the plasma fall to as low as 25% of non-pregnant levels. This suggests there is an increased utilization of pyridoxine during gestation. Vitamin $B_6$ and folic acid have been shown to be associated with the lower risk of coronary artery disease particularly among women. While Vitamin $B_6$ is present in meat, whole grain breads and cereals as well as vegetables, it is particularly diminished among patients at high risk for inadequate nutrition (substance abuse, adolescents, short intervals between pregnancies, multi-fetal pregnancies, and women on restricted intake such as vegan diets). Among animals, Vitamin $B_6$ deficiency during pregnancy is associated with severe growth retardation, hypoplasia of the thymus and neonatal death as well as reduced immunologic competence. While there is no direct evidence of adverse effects of such deficiency in humans, volunteer studies among non-pregnant adults have shown that Vitamin $B_6$ deficiency can cause skin manifestations and some central nervous system defects. Further low levels tend to persist after pregnancy and during lactation and are also lower in cord blood and in the milk of such women. The present invention includes about 20 mg/day to about 50 mg/day, in varying amounts during the three trimesters, such as about 50 mg/day during the first trimester, about 25 mg/day during the second trimester, and about 20 mg/day during the third trimester.

Vitamin $B_{12}$ is essential for appropriate folic acid metabolism, a deficiency of which is noted by megaloblastic anemia. It also plays a role in maintaining cellular integrity of the central nervous system. Therefore, while supplementation of folic acid may cure hematologic symptoms (anemia) of $B_{12}$ deficiency, it will leave the fetus vulnerable to central nervous system damage. Vitamin $B_{12}$ is found exclusively in animal tissues hence during pregnancy a vegan woman is at risk for $B_{12}$ deficiency. Accordingly, the present invention includes about 2 mcg/day to about 12 mcg/day of Vitamin $B_{12}$, preferably about 2 mcg/day (0.002 mg/day), as cyanocobalamin, to mitigate any deficiency of this essential vitamin.

Vitamin C (ascorbic acid) is essential for the formation of collagen and therefore is very important for both mother and fetus during pregnancy. The transport mechanism across the placenta is the same for that of glucose therefore Vitamin C supplementation is very important in those women having (or at risk for) diabetes. There is a progressive drop in Vitamin C levels during each trimester and if serum levels of this ingredient drop below 80 mg/day habitual abortion, preterm birth and preterm rupture of the membranes may occur. Since there are vagaries of absorption during pregnancy, the present invention includes about 20 mg/day to about 200 mg/day, preferably about 60 mg/day, of Vitamin C supplementation.

Vitamin $D_3$ (cholecalciferol) regulates calcium homeostasis by maintaining equilibrium (along with parathormone) between calcium resorption and excretion. If Vitamin $D_3$ levels are low, then the mother may lose significant calcium in her urine. If maternal calcium intake is low, then poor bone mineralization is likely to occur in infants. The present invention includes about 200 to about 500 IU, preferably about 400 IU (10 mcg)/day, of Vitamin $D_3$ to mitigate these problems in the mother and fetus. Each IU of Vitamin $D_3$ corresponds to 0.025 mcg.

Vitamin E is stored in fat and since the majority of fetal fat deposition occurs after 36 weeks' gestation, the deficiency is very likely to occur in any infant born preterm. Therefore, this is a particularly important ingredient of a prenatal supplement when there is or may be a risk of preterm delivery. Since early births cannot be predicted (occurring from preterm labor as well as medical/surgical complications) the present invention includes about 10 to about 40 mg/day of Vitamin E, as natural a-tocopherol, regardless of dietary sufficiency. Increasing amounts are used starting with about 10 mg/day during the first trimester, about 20 mg/day during the second trimester, and about 30 mg/day during the third trimester. Optionally, the synthetic form of a-tocopherol can be used in equivalent amounts.

Low levels of lycopene as well as other anti-oxidants are noted to be present in the placenta and fetuses of women with preterm labor, fetal growth restriction, and pre-eclampsia (pregnancy-induced hypertension). Lycopene content is high in tomatoes, but not in other vegetables, thus unless a woman's diet is rich in tomato or tomato-based products there may be a deficiency of this important ingredient. Thus, the present invention includes about 100 mg/day to about 500 mg/day of a lycopene-containing material for prenatal women at risk for oxidative stress. As commercially available lycopene materials generally have only about 5% to about 10% lycopene, the actual lycopene in the supplements of the present invention will be about 5 mg/day to about 25 mg/day of lycopene, preferably about 5 mg/day to about 10 mg/day. The present invention includes varying amounts of, lycopene during the three trimesters, such as about 5 mg/day during the first trimester, about 10 mg/day during the second trimester, and about 5 mg/day during the third trimester, stated as lycopene content.

Cotho (Co-enzyme $Q_{10}$) is an anti-oxidant that is deficient in the serum of many women with pre-eclampsia. The activity of $CoQ_{10}$ is directed against free radical damage to the endothelial cells lining blood vessels; an abnormality frequently observed in pre-eclampsia. This allows the normal vasodilatation during pregnancy thought to be mediated through nitric oxide. This anti-oxidant works well with Vitamin C in preventing such endothelial damage. Thus, the present invention includes of $CoQ_{10}$ in about 50 mg/day to about 200 mg/day, in varying amounts during the three trimesters, such as about 200 mg/day during the first trimester, and about 150 mg/day during each of the second and third trimesters, to enhance the function of Vitamin C and other free radical scavengers.

Omega-3 fatty acids found in marine fats have been shown to be important in the prevention of pre-eclampsia, preterm delivery and early rupture of the membranes. Enhanced, cognitive function and improved visual acuity in babies born to mothers supplemented with docosahexaenoic acid (DHA) have also been noted. Finally, there has been a decrease in maternal postpartum depression when supplemented with DHA. Cold water fish are the highest dietary sources of DHA and it is also available in the eggs of chickens supplemented with micro-algae. Unfortunately, supplementation from these two sources is rare in this country and, therefore, the present invention includes about 50 mg/day to about 250 mg/day, preferably about 100 mg/day to about 200 mg/day, of DHA, which is a beneficial amount for pregnant women. Increasing amounts are used starting with 100 mg/day during the first trimester, 150 mg/day during the second trimester and 200 mg/day during the third trimester. Optionally, also slightly less preferred, a uniform amount of 200 mg/day of DHA can be used in each supplement of this invention.

The small and large intestine become sluggish during pregnancy due to high levels of progesterone. Even in the presence of adequate amounts of water, constipation is a tremendous problem in most pregnant women, particularly during the last two trimesters of pregnancy. Iron supplementation (ferrous sulfate and ferrous fumarate) while useful for the mother and developing fetus also increases the chance of constipation and, therefore, the present invention includes about 50 mg/day to about 100 mg/day of docusate sodium, to help mitigate this annoying, and not to be ignored, problem. Increasing amounts are used starting with about 50 mg/day during the first trimester, about 75 mg/day during the second trimester, and about 100 mg/day during the third trimester.

Of all the trace elements, copper has received attention as probably being the most important in human gestation. The metabolism of this element is more altered by pregnancy than any other state. While serum copper rises during pregnancy, due to hormonal changes and protein binding efficiency, levels of copper are low in the fetus; therefore, it is important to supplement this trace element in the diet of pregnant women. Copper is also important as it is associated with a protein in the fetal mitochondria, which disappears shortly after birth. This mitochondrial function is important in most oxidative reactions in rapidly developing fetal tissues. The present inventions includes about 1 mg/day to about 3 mg/day, preferably about 2 mg/day, of copper throughout the pregnancy to ensure that pregnant women have appropriate levels of copper during these important stages.

Folic acid is probably the most important vitamin during pregnancy. The requirement increases significantly in pregnancy and a deficiency of this vitamin is prevalent among American women. The cardinal result of folic acid deficiency is a maternal anemia that is significantly increased during pregnancy. It has been estimated that 2.5 to 5% of pregnant women in the United States are folic acid-deficient and this is particularly true in indigent patients, adolescents, or those having successive pregnancies with short intervals between them. A deficiency of folic acid results in fetal neural tube defects, preterm delivery, placental abruption and growth restricted fetuses. Since foods in this country are not fortified with folic acid, the present invention includes about 1 mg/day to about 5 mg/day, increasing from about 1 mg/day during the first trimester, to about 2 mg/day during the second trimester, and then 3 mg/day during the third trimester.

Because of the blood formation requirements of the fetus and placenta, iron depletion and iron deficiency anemia make this the most common deficiency in pregnancy (90% of all anemias). Heme iron, which is derived from hemoglobin and myoglobin found in meats, is much better absorbed than non-heme, which is found mostly in foods of plant origin (30% versus 5% absorption). People who are vegetarians absorb much less iron than needed during pregnancy. Growth restriction, preterm delivery, and pre-eclampsia have been noted in women who have iron deficiency. One of the problems with iron supplementation is upper GI irritation resulting in nausea, vomiting and a decreased appetite as well as constipation. Thus, the present invention includes about 30 mg/day to about 90 mg/day of elemental iron content, preferably as carbonyl iron that has just under 100% iron content, to mitigate both of these problems. Other pharmaceutically or nutritionally acceptable iron-containing compounds may be used in the supplements of the present invention, for example ferrous fumarate, ferrous sulfate, etc. The amount of the iron-containing compound used will be the amount that will give about 30 mg/day to about 90 mg/day of elemental iron content. Thus, for example, if using ferrous fumarate that has about 33% iron content, then about 90 mg/day to about 270 mg/day of the ferrous fumarate should be used. Increasing amounts are used starting with about 30 mg/day during the first trimester, about 45 mg/day during the second trimester, and about 60 mg/day during the third trimester.

Magnesium deficiency has been linked to pre-eclampsia, preterm rupture of the membranes and preterm births secondary to early labor. Women who deliver preterm are more likely to have lower plasma levels of this mineral. The present invention includes about 10/mgday to about 100 mg/day of magnesium to supplement any deficiencies that may occur. Varying amounts are used starting with about 30 mg/day during the first trimester, and about 50 mg/day during each of the second and third trimesters.

Selenium deficiency like iron deficiency and zinc deficiency is common during pregnancy. Low selenium levels have been reported in patients with habitual abortions and in women with pre-eclampsia and cardiomyopathy. Since this mineral is an essential ingredient of the enzyme glutathione peroxidase, it is an important defensive ingredient against free radical damage in blood vessels and the developing fetus. Selenium is a trace element that has the ability to remove hydroperoxides and oxidized lipoproteins. Moreover, selenoprotein is able to scavenge peroxynitrite on the surface of vascular endothelium thus highlighting its role in pre-eclampsia. The present invention includes about 10 mcg/day to about 30 mcg/day, preferably about 15 mcg/day, of selenium throughout the pregnancy to mitigate these problems.

Zinc deficiency produces congenital malformations as well as fetal losses. Since maternal plasma levels of zinc decrease during pregnancy, supplementation is important. In the fetus deficiency of zinc may be involved with premature rupture of the membranes and a reduced ability to fight infection due to suppressed immunity. Zinc deficiency is quite common in the United States, particularly in pregnant women and, therefore, the present invention includes about 15 mg/day to about 30 mg/day of zinc. Varying amounts are used starting with about 15 mg/day during the first trimester, and about 30 mg/day during each of the second and third trimesters.

All of the ingredients of the present invention are well known and are commercially available, generally from multiple sources. They may be used in any chemical form known in the art to be suitable for use in nutritional supplements, except that, in certain instances set forth above, particularly with regard to the preferred and particularly preferred embodiments of the present invention, specific forms are desired, as with beta-carotene for Vitamin A and carbonyl iron for the iron ingredient of the present invention. In addition, the methods of manufacture thereof are well known to those skilled in this art and need not be described further herein.

The compositions of the present invention include any suitable pharmaceutically or nutritionally acceptable carrier as would be known to one skilled in this art. The methods of pharmaceutical formulation applicable to the supplements of the present invention are also well known to one skilled in this art and need not be described further herein. Suitable carriers and methods of formulation are shown, for example, in the Hermelin et al. and Cooper et al. patents cited above and, to the extent necessary, the disclosures thereof pertaining thereto are incorporated herein by this reference. Any dosage form may be utilized as desired, although, given the nature of the ingredients described herein, oral dosage forms, such as a conventional tablet, using conventional pharmaceutically or nutritionally acceptable tablet ingredients, is satisfactory and is the preferred form of administration, although other dosage forms, such as caplets or chewable tablets, may be used as well. A single daily tablet taken orally will suffice, generally to be taken at breakfast so as not to be forgotten during the day, although if desired, smaller tablets can be utilized, for example, ones with one-half or one-third the daily dosage to be taken, for example, at other or each mealtimes, or after pregnancy-induced nausea may have subsided. If the daily tablet is considered too large for ease of ingestion, the tablet may be scored so as to be broken in half and taken one after the other or at different times during the day or a chewable tablet can be used. The DHA can also be in its own dosage form (generally a separate tablet or capsule), which can be taken at the same time as the other ingredients or at a different time if so desired. These supplements are particularly suited for being administered to, or to be taken by, pregnant women and are free of any other added vitamins and minerals, and other unnecessary ingredients, such as N-acetyl-cysteine.

EXAMPLES

Example 1

The following embodiment of the present invention is prepared as an oral tablet to be taken once daily during the first trimester of pregnancy to supplement the nutritional diet of a pregnant woman:

2,500 IU (1.5 mg) of Vitamin A (as beta-carotene),
2 mg of Vitamin $B_1$,
3.4 mg of Vitamin $B_2$,
50 mg of Vitamin $B_6$,
2 mcg of Vitamin $B_{12}$,
60 mg of Vitamin C,
400 IU (10 mcg) of Vitamin $D_3$,
15 IU (10 mg) of Vitamin E,
100 mg of a 5% lycopene-containing material (corresponding to about 5 mg of actual lycopene),
200 mg of co-enzyme Q10,
100 mg of docosahexaenoic acid (DHA),
50 mg of docusate sodium,
2 mg of copper,
1 mg of folic acid,
30 mg of elemental iron (as carbonyl iron),
30 mg of magnesium,
15 mcg of selenium, 15 mg of zinc, and a pharmaceutically or nutritionally acceptable carrier therefor.

Example 2

The following embodiment of the present invention is prepared as an oral tablet to be taken once daily during the second trimester of pregnancy to supplement the nutritional diet of a pregnant woman:

2,500 IU (1.5 mg) of Vitamin A (as beta-carotene),
2 mg of Vitamin $B_1$,
3.4 mg of Vitamin $B_2$,
25 mg of Vitamin $B_6$,
2 mcg of Vitamin $B_{12}$,
60 mg of Vitamin C,
400 IU (10 mcg) of Vitamin $D_3$,
30 IU (20 mg) of Vitamin E,
200 mg of a 5% lycopene-containing material (corresponding to about 10 mg of actual lycopene),
150 mg of co-enzyme Q10,
150 mg of docosahexaenoic acid (DHA),
75 mg of docusate sodium,
2 mg of copper,
2 mg of folic acid,
45 mg of elemental iron (as carbonyl iron),
50 mg of magnesium,
15 mcg of selenium,
30 mg of zinc, and
a pharmaceutically or nutritionally acceptable carrier therefor.

Example 3

The following embodiment of the present invention is prepared as an oral tablet to be taken once daily during the third trimester of pregnancy to supplement the nutritional diet of a pregnant woman:

2,500 IU (1.5 mg) of Vitamin A (as beta-carotene),
2 mg of Vitamin $B_1$,
3.4 mg of Vitamin $B_2$,
20 mg of Vitamin $B_6$,
2 mcg of Vitamin $B_{12}$,
60 mg of Vitamin C,
400 IU (10 mcg) of Vitamin $D_3$,
45 IU (30 mg) of Vitamin E,
100 mg of a 5% lycopene-containing material (corresponding to about 5 mg of actual lycopene),
150 mg of co-enzyme Q10,
200 mg of docosahexaenoic acid (DHA),
100 mg of docusate sodium,
2 mg of copper,
3 mg of folic acid,
60 mg of elemental iron (as carbonyl iron),
50 mg of magnesium,
15 mcg of selenium,
30 mg of zinc, and
a pharmaceutically or nutritionally acceptable carrier therefor.

The embodiments of the present invention can be or are, as shown above in the Examples, substantially free of other added vitamins and minerals.

The tablets of each of the above Examples can be scored to be broken in half for ease of self-administration if desired. Optionally, the daily dose can be split between two or three tablets to be taken at various times (for example, at meal times) during the day, or chewable tablets can be used.

While various embodiments of the present invention have been described, it should be understood that various modifications and adaptations thereof will be apparent to one skilled in this art. Such modifications and adaptations are considered to be within the scope of the present invention, which is limited only by the scope of the following claims.

What is claimed is:

1. A nutritional supplement consisting essentially of a daily dose of:
   about 2,000 to about 8000 IU of Vitamin A,
   about 1 to about 5 mg of Vitamin $B_1$,
   about 1 to about 15 mg of Vitamin $B_2$,
   about 20 to about 50 mg of Vitamin $B_6$,
   about 2 to about 12 mcg of Vitamin $B_{12}$,
   about 20 to 200 mg of Vitamin C,
   about 200 to about 500 IU of Vitamin $D_3$,
   about 10 to about 40 mg of Vitamin E,
   about 5 mg to about 25 mg of lycopene,
   about 50 to about 200 mg of co-enzyme Q10,
   about 50 to about 250 mg of docosahexaenoic acid,
   about 50 to about 100 mg of docusate sodium,
   about 1 to 3 mg of copper,
   about 1 to about 5 mg of folic acid,
   about 30 to about 90 mg of elemental iron,
   about 10 to about 100 mg of magnesium,
   about 10 to about 30 mcg of selenium,
   about 15 to about 30 mg of zinc, and
   a nutritionally acceptable carrier therefor,
   wherein said supplement is suited for being administered to, or to be taken by, a pregnant woman and is substantially free of other added vitamins and minerals.

2. The supplement of claim 1 wherein the Vitamin A is present in the amount of about 2,500 IU.

3. The supplement of claim 1 wherein the Vitamin $B_1$ is present in the amount of about 2 mg.

4. The supplement of claim 1 wherein the Vitamin $B_2$ is present in the amount of about 3.4 mg.

5. The supplement of claim 1 wherein the Vitamin $B_6$ is present in the amount of about 20 mg, 25 mg, or 50 mg.

6. The supplement of claim 1 wherein the Vitamin $B_{12}$ is present in the amount of about 2 mcg.

7. The supplement of claim 1 wherein the Vitamin C is present in the amount of about 60 mg.

8. The supplement of claim 1 wherein the Vitamin $D_3$ is present in the amount of about 400 IU.

9. The supplement of claim 1 wherein the Vitamin E is present in the amount of about 10 mg, 20 mg, or 30 mg.

10. The supplement of claim 1 wherein the lycopene is present in the amount of about 5 mg of lycopene to about 10 mg of lycopene.

11. The supplement of claim 1 wherein the co-enzyme Q10 is present in the amount of about 150 mg or 200 mg.

12. The supplement of claim 1 wherein the docosahexaenoic acid is present in the amount of about 100 mg, 150 mg, or 200 mg.

13. The supplement of claim 1 wherein the docusate sodium is present in the amount of about 50 mg, 75 mg or 100 mg.

14. The supplement of claim 1 wherein the copper is present in the amount of about 2 mg.

15. The supplement of claim 1 wherein the folic acid is present in the amount of about 1 mg, 2 mg or 3 mg.

16. The supplement of claim 1 wherein the elemental iron is present in the amount of about 30 mg, 45 mg, or 60 mg.

17. The supplement of claim 1 wherein the magnesium is present in the amount of about 30 mg or 50 mg.

18. The supplement of claim 1 wherein the selenium is present in the amount of about 15 mcg.

19. The supplement of claim 1 wherein the zinc is present in the amount of about 15 mg or 30 mg.

20. A nutritional supplement consisting of a daily dose of:
about 2,500 IU of Vitamin A,
about 2 mg of Vitamin $B_1$,
about 3.4 mg of Vitamin $B_2$,
about 50 mg of Vitamin $B_6$,
about 2 mcg of Vitamin $B_{12}$,
about 60 mg of Vitamin C,
about 400 IU of Vitamin $D_3$,
about 15 IU of Vitamin E,
about 5 mg of lycopene,
about 200 mg of co-enzyme Q10,
about 100 mg of docosahexaenoic acid,
about 50 mg of docusate sodium,
about 2 mg of copper,
about 1 mg of folic acid,
about 30 mg of elemental iron,
about 30 mg of magnesium,
about 15 mcg of selenium,
about 15 mg of zinc, and
a nutritionally acceptable carrier therefor,
wherein said supplement is suited for being administered to, or to be taken by, a pregnant woman during her first trimester of pregnancy.

21. The nutritional supplement of claim 20 wherein the daily dose is split between two tablets that are self-administered by the woman during a twenty-four hour period.

22. The nutritional supplement of claim 20 wherein the supplement is in the form of a scored tablet that optionally can be broken in half for ease of self-administration by the woman.

23. A nutritional supplement consisting of a daily dose of:
about 2,500 IU of Vitamin A,
about 2 mg of Vitamin $B_1$,
about 3.4 mg of Vitamin $B_2$,
about 25 mg of Vitamin $B_6$,
about 2 mcg of Vitamin $B_{12}$,
about 60 mg of Vitamin C,
about 400 IU of Vitamin $D_3$,
about 30 IU of Vitamin E,
about 10 mg of lycopene,
about 150 mg of co-enzyme Q10,
about 150 mg of docosahexaenoic acid,
about 75 mg of docusate sodium,
about 2 mg of copper,
about 2 mg of folic acid,
about 45 mg of elemental iron,
about 50 mg of magnesium,
about 15 mcg of selenium,
about 30 mg of zinc, and
a nutritionally acceptable carrier therefor,
wherein said supplement is suited for being administered to, or to be taken by, a pregnant woman during her second trimester of pregnancy.

24. The nutritional supplement of claim 23 wherein the daily dose is split between two tablets that are self-administered by the woman during a twenty-four hour period.

25. The nutritional supplement of claim 23 wherein the supplement is in the form of a scored tablet that optionally can be broken in half for ease of self-administration by the woman.

26. A nutritional supplement consisting of a daily dose of:
about 2,500 IU of Vitamin A,
about 2 mg of Vitamin $B_1$,
about 3.4 mg of Vitamin $B_2$,
about 20 mg of Vitamin $B_6$,
about 2 mcg of Vitamin $B_{12}$,
about 60 mg of Vitamin C,
about 400 IU of Vitamin $D_3$,
about 45 IU of Vitamin E,
about 5 mg of lycopene,
about 150 mg of co-enzyme Q10,
about 200 mg of docosahexaenoic acid,
about 100 mg of docusate sodium,
about 2 mg of copper,
about 3 mg of folic acid,
about 60 mg of elemental iron,
about 50 mg of magnesium,
about 15 mcg of selenium,
about 30 mg of zinc, and
a nutritionally acceptable carrier therefor,
wherein said supplement is suited for being administered to, or to be taken by, a pregnant woman during her third trimester of pregnancy.

27. The nutritional supplement of claim 26 wherein the daily dose is split between two tablets that are self-administered by the woman during a twenty-four hour period.

28. The nutritional supplement of claim 26 wherein the supplement is in the form of a scored tablet that optionally can be broken in half for ease of self-administration by the woman.

29. A method of supplementing the daily nutritional diet of a pregnant woman comprising administering to such a woman the supplement of claim 1.

30. A method of supplementing the daily nutritional diet of a pregnant woman comprising orally administering to such a woman once during a twenty-four hour period the supplement of claim 1.

31. A method of supplementing the daily nutritional diet of a pregnant woman comprising orally administering to such a woman two or three times during a twenty-four hour period, in the aggregate, the amounts of the ingredients set forth in the supplement of claim 1.

32. A method of supplementing the daily nutritional diet of a pregnant woman comprising administering to such a woman the supplement of claim 20 during the first trimester of her pregnancy.

33. A method of supplementing the daily nutritional diet of a pregnant woman comprising administering to such a woman the supplement of claim 23 during the second trimester of her pregnancy.

34. A method of supplementing the daily nutritional diet of a pregnant woman comprising administering to such a woman the supplement of claim 26 during the third trimester of her pregnancy.

35. A nutritional supplement regimen consisting essentially of a set of three differing nutritional supplements for administration to, or to be taken by, a pregnant woman during the three trimesters of her pregnancy, wherein the respective amounts of each of Vitamins A, $B_1$, $B_2$, $B_{12}$, C, and D3, copper and selenium are essentially the same in each of the three nutritional supplements; the respective amounts of each of Vitamin E, docosahexaenoic acid, docusate sodium, folic acid and iron are the lowest in the nutritional supplement for the first trimester, the highest in the nutritional supplement for the third trimester, with an intermediate amount in the nutritional supplement for the second trimester; the respective amounts of each of magnesium and zinc are the lowest in the nutritional supplement for the first trimester and are higher in the nutritional supplements for the second and third trimesters; the amount of Vitamin B6 is the highest in the nutritional supplement for the first trimester, the lowest in the nutritional supplement for the third trimester, with an intermediate amount in the nutritional supplement for the second trimester; the amount of co-enzyme Q10 is the highest in the nutritional supplement for the first trimester and lower in the nutritional supplements for the second and third trimesters; and the amount of lycopene is lower in the nutritional supplements for the first and third trimesters than it is in the nutritional supplement for the second trimester.

36. The nutritional regimen of claim 35 wherein the respective amounts of magnesium and zinc in the nutritional supplement for the second trimester are essentially the same as the respective amounts therefor in the nutritional supplement for the third trimester.

37. The nutritional regimen of claim 35 wherein the amounts of co-enzyme Q-10 in the nutritional supplements for the second and third trimesters are essentially the same.

38. The nutritional regimen of claim 35 wherein the amounts of lycopene in the nutritional supplements for the first and third trimesters are essentially the same.

39. The nutritional regimen of claim 35 wherein the amounts of folic acid are at least about 1 mg in the supplements for each of the three trimesters.

40. The nutritional regimen of claim 35 wherein the amount of folic acid in the nutritional supplement for the first trimester is about 1 mg, the amount of folic acid in the nutritional supplement for the second trimester is about 2 mg, and the amount of folic acid in the nutritional supplement for the third trimester is about 3 mg.

41. A method of supplementing the daily nutritional diet of a pregnant woman comprising administering to such a woman the supplements of claim 35 during the first, second and third trimesters of her pregnancy.

42. A method of supplementing the daily nutritional diet of a pregnant woman comprising administering to such a woman the supplements of claim 39 during the first, second and third trimesters of her pregnancy.

43. A method of supplementing the daily nutritional diet of a pregnant woman comprising administering to such a woman the supplements of claim 40 during the first, second and third trimesters of her pregnancy.

* * * * *